United States Patent [19]

Schuster et al.

[11] 4,288,640

[45] Sep. 8, 1981

[54] CARRYING OUT EXOTHERMIC REACTIONS BETWEEN A GAS AND A LIQUID

[75] Inventors: Ludwig Schuster; Paul Raff, both of Ludwigshafen; Herwig Hoffmann, Frankenthal; Rolf Schneider, Mannheim; Erich Flickinger, Frankweiler, all of Fed. Rep. of Germany

[73] Assignee: BASF Aktiengesellschaft, Ludwigshafen, Fed. Rep. of Germany

[21] Appl. No.: 707,499

[22] Filed: Jul. 22, 1976

Related U.S. Application Data

[63] Continuation of Ser. No. 63,068, Aug. 12, 1970, abandoned.

[30] Foreign Application Priority Data

Aug. 16, 1969 [DE] Fed. Rep. of Germany ....... 1941633

[51] Int. Cl.$^3$ ............... C07C 33/046; C07C 33/042; C07C 39/08; C07C 87/52
[52] U.S. Cl. .................................... 568/855; 568/772; 568/807; 568/813; 568/874; 260/690; 260/694
[58] Field of Search ................. 260/635 Y, 690; 568/855, 874, 772, 807, 813; 564/420, 422

[56] References Cited

U.S. PATENT DOCUMENTS 3,154,589 10/1964 Moore ............................ 260/635 Y
3,565,921 2/1971 Gibson et al. .................... 260/638 B

OTHER PUBLICATIONS

Alien Property Custodian, S.N. 327,820, Reppe et al. (1943).
Weekman et al., "A.I.E.C. Journal", vol. 10, (1964), pp. 951–957.
Weissberger, "Technique of Organic Chemistry", vol. III, Part II, pp. 235–239, 267–268, (1957).

Primary Examiner—Joseph E. Evans
Attorney, Agent, or Firm—Keil & Witherspoon

[57] ABSTRACT

Process for carrying out exothermic reactions between a gas and a liquid in the presence of a solid catalyst by passing the gas and the liquid cocurrently through a packed reaction vessel, preferably of elongated shape, wherein the gas and liquid pass through the packed reaction vessel in transition flow.

13 Claims, 3 Drawing Figures

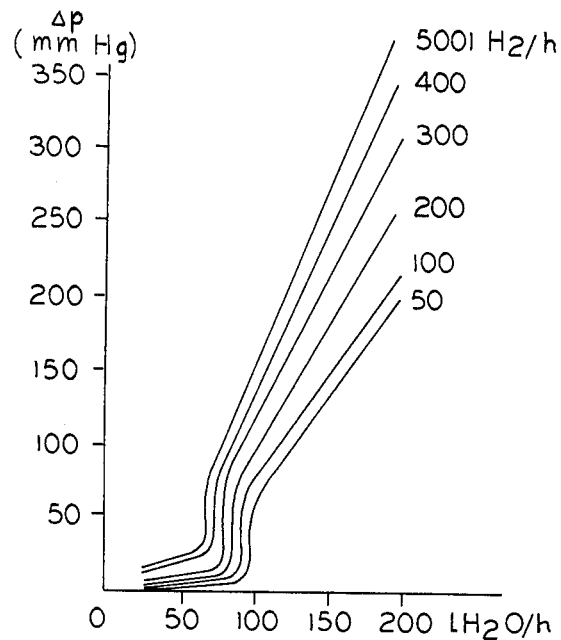
FIG. 1
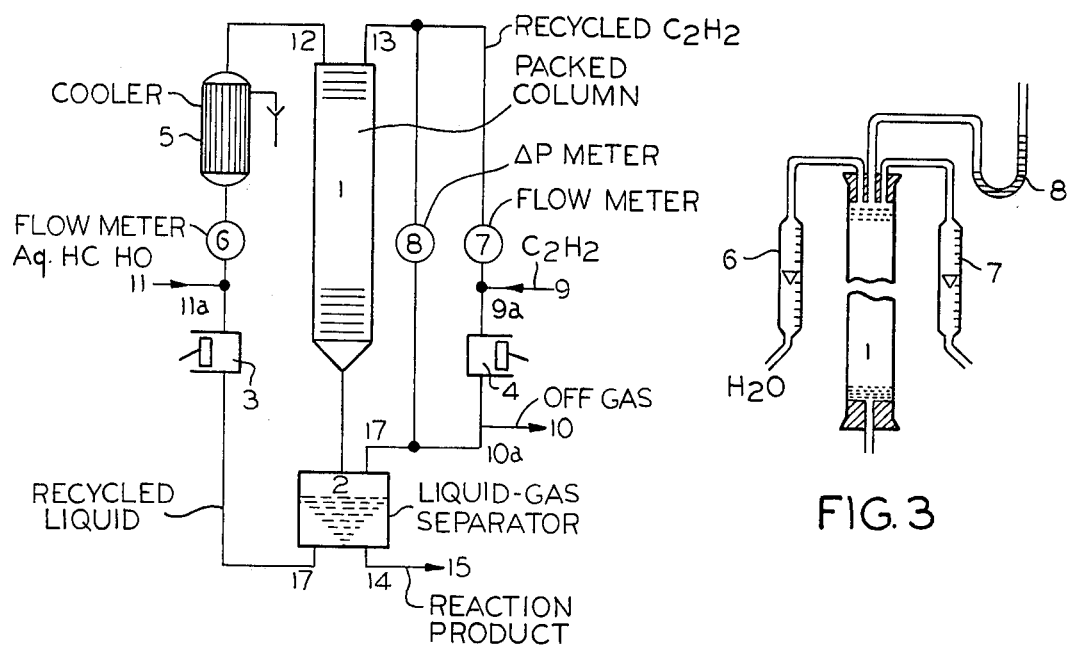
FIG. 2
FIG. 3

CARRYING OUT EXOTHERMIC REACTIONS BETWEEN A GAS AND A LIQUID

RELATED APPLICATION

This application is a continuation of our application Ser. No. 63,068, filed Aug. 12, 1970, now abandoned.

It is known that exothermic reactions between gases and liquids with formaldehyde to form butynediol (of. Ullmanns Encyclopädie der technischen Chemie, volume 3 (1953), pages 109 to 119), can be carried out in such a way that the liquid trickles over the catalyst used as a packing in a packed column while at the same time the gas is passed through cocurrently. In this method, however, only a poor space-time yield is achieved. Byproducts are formed very readily and/or the catalyst is easily damaged because of the occurrence of local over-heating due to the difficulty of removing heat.

It is known from *A.I.Ch.E. Journal*, volume 10 (1964), pages 951 to 957, that when air and a water are passed cocurrently through a packed column (i.e. a column containing glass beads) the following types of flow occur depending on the loading of the column by air and water:

(1) In the region of gas continuous flow, the liquid trickles over the tower packing and the gas phase flows continuously through the voids in the packing. The liquid flows as a laminar film over the individual packing bodies.

(2) In the region of transition flow, the liquid moves through the packing in a type of turbulent flow.

(3) In pulsing flow, pulses in the form of waves of higher density pass through the packed column at a specific frequency.

We have now found that exothermic reactions between a gas and a liquid in the presence or a solid catalyst in which the gas and the liquid are passed cocurrently through a packed reaction vessel, preferably of elongated shape, can be carried out advantageously by passing the gas and liquid through the packed reaction vessel in transition flow, which is defined below.

In the new process an intimate mixture of gas and liquid flows through the bed of packing. The reaction products from the gas and liquid are therefore obtained in a considerably higher space-time yield than in production by the conventional method, which is carried out in the region of gas continuous flow. The heat of reaction may be removed very easily without the occurrence of hot spots. The formation of byproducts is thus substantially prevented so that the reaction products are obtained in higher purity than according to prior art processes.

The gas used as starting material, such as carbon dioxide, carbon monoxide, ethylene, hydrogen, acetylene and oxygen may be used as such or diluted with inert gas such as nitrogen. The liquid starting material may also be used alone or in admixture with liquids which are inert under the reaction conditions, for example organic solvents or the reaction product itself. The liquid may also be a solution of a solid or gaseous starting material in an inert solvent.

The exothermic reaction between gas and liquid is carried out in the presence of a solid catalyst. The catalyst may be used as such or, after application to an inert carrier material, as a supported catalyst. The catalyst generally serves at the same time as the tower packing. It is possible however to use inert packing in addition to the catalytically active tower packing. The tower packing may be for example in the form of spheres, rings, cylinders or tablets. When spheres are used, they generally have a diameter of from 2 to 8 mm. Cylindrical tower packing is usually from 2 to 15 mm in length and from 2 to 6 mm in diameter. Tower packing which is not spherical or cylindrical generally has a volume roughly equivalent to that of the spherical tower packing.

The process is particularly suitable for exothermic reactions between a gas and a liquid in the presence of a solid catalyst where a narrow temperature range has to be maintained, i.e. for reactions in which the occurrence of fluctuations in temperature during the reaction or the occurrence of hot spots have proved to be unfavorable. A narrow temperature range is taken to mean a range of fluctuation of ±20° C., preferably of ±5° C. The process may therefore be used with particular advantage for example for catalytic hydrogenation and for the ethynylation reaction. Other suitable reactions include the oxidation of hydrocarbons, such as cyclohexane or p-xylene, with molecular oxygen and the halogenation of hydrocarbons. When the new process is used for individual reactions, the general reaction conditions, such as the use of solid catalyst or the temperature are generally not affected. The more rapid and more intense mixing of gas and liquid brought about by the new process can however be of influence on the speed of reaction and it may be advantageous, on the basis of the new higher reaction speed, to re-optimize the process parameters, such as mean residence time, temperature and amount of catalyst, which have proved to be optimal in an industrial process.

It is an essential feature of the new process that the gas and liquid should be passed through the packed reaction vessel in transition flow. Contrary to the results described in *A.I.Ch.E. Journal*, volume 10 (1964), pages 952 to 953, according to which there is no sharp variation in the pressure difference $\Delta p$ between the point of supply of water to the packed column and the point of withdrawal of the water from the column in the transition from gas continuous flow to transition flow and from transition flow to pulsing flow, we have found that the transition from gas continuous flow to transition flow is characterized by a sudden increase in the pressure difference $\Delta p$ (as shown in FIG. 1).

The occurence of transition flow may for example be done by visual inspection and/or by measurement of the pressure difference $\Delta p$. Transition flow may be observed visually for example by occurence of turbulence of liquid flow in the column, e.g., as in *A.I.Ch.E. Journal*, volume 10 (1964), pages 952 to 953. The start of transition flow by measuring the pressure difference $\Delta p$ may be carried out for example by adjusting the gas loading required for the reaction (measured in parts by volume (STP) per unit time) and, beginning at a loading L of the reaction vessel with liquid (measured in parts by volume per unit time) of about zero, passing increasing amounts of liquid through the reaction vessel. The region of gas continuous flow is first traversed, and this region is characterized by an almost linear slow rise in the pressure difference $\Delta p$ as load L increases. Upon further increasing the liquid loading L, the beginning of the region of transition flow is indicated by a sudden increasingly steeper rise in the pressure difference $\Delta p$. Generally the region of transition flow is reached when the rise in the pressure difference $\Delta p$ with increasing load L, expressed as $(\Delta p)/L$, is at least twice, preferably three times, the average rise in the region of gas continuous flow. When the liquid loading L is increased further, the rise becomes linear again, but is now considerably steeper than in the region of gas continuous flow (cf. FIG. 1). When the liquid loading L is further increased, the region of transition flow is left and the region of pulsing flow is entered, which is characterized by fluctuations in the pressure difference $\Delta p$ caused by the pulses. The fluctuations have about the same frequency as the pulses.

It is advantageous to use reaction vessels of elongated shape for the process according to this invention. The vessels may have any cross section, e.g. a square or elliptical cross section. In general, cylindrical reaction vessels are used. The ratio of diameter to length of the vessel is as a rule from 1:2 to 1:60, preferably from 1:10 to 1:40. The vessels may be arranged vertically or horizontally or inclined. Vertical vessels are preferred.

The process according to the invention may be carried out batchwise or continuously. When using columns conventionally used in industry, complete conversion is generally not achieved in a single passage of the liquid. In this case the liquid is advantageously recycled more than once, for example from three to thirty times, through the packed column. It is also possible however to achieve complete conversion in a single passage of the liquid by using very long narrow packed columns, for example packed columns whose ratio of diameter to length is from 1:50 to 1:100.

Continuous operation of the process may be carried out for example by recycling the reaction mixture through the packed vessel, the starting materials being fed into the recycled reaction mixture prior to entry into the reaction vessel and the reaction product being removed from the recycled reaction mixture after it has left the reaction zone. Continuous operation may also be carried out by allowing the reaction mixture to flow through several, for example three to five, successive recycle apparatus.

When using the new process for the ethynylation reaction, i.e. the production of alkynols and/or alkynediols by reaction of acetylene with aldehydes in the presence of a heavy metal acetylide (a heavy metal being defined as a metal having a specific gravity of more than 5) and in the presence or absence of basic reagents, acetylides of heavy metals of the first or second group of the Periodic System are usually used as solid catalysts. Heavy metal acetylides may be used as such for the reaction. It is possible however to use the heavy metals themselves or their salts which are then converted into the corresponding acetylides at the beginning of the reaction. Examples of suitable heavy metals are silver, gold, mercury and particularly copper. When using heavy metal salts, the nature of the anion is not critical. Examples of heavy metal salts which may be used are copper phosphate, copper acetate, copper(I) chloride, copper(II) chloride, copper acetate, copper formate, silver nitrate and mercury chloride. The heavy metal acetylides are preferably used after they have been applied to shaped carrier material which acts as the same time as as tower packing. Examples of suitable carrier materials are aluminum oxide, animal charcoal, diatomaceous earth and particularly silica gel.

Ethynylation is advantageously carried out in the presence of an inert solvent or diluent such as an alcohol, ether, ester, carbonamide, aromatic or aliphatic hydrocarbon or water. Specific examples are ethanol, isobutanol, n-butanol, ethyl glycol, dioxane, tetrahydrofuran, dimethylformamide and N-methylpyrrolidone. The end product itself or excess liquid starting material may also serve as diluent.

Alkylacetylenes, preferably those having three to six carbon atoms, arylacetylenes, preferably those having up to twelve carbon atoms, and alkenyl or alkynyl acetylenes preferably having four to six carbon atoms and particularly acetylene itself are used for the ethynylation. Examples are methylacetylene, ethylacetylene, phenylacetylene, vinylacetylene and diacetylene.

Aromatic aldehydes preferably having up to eleven carbon atoms and particularly aliphatic aldehydes are used for the ethynylation. The aliphatic aldehydes generally have one to twelve, preferably one to six, carbon atoms. Examples of suitable aldehydes are acetaldehyde, butyraldehyde, n-caproaldehyde, benzaldehyde and preferably formaldehyde. Formaldehyde may be used in monomeric form, for example as commercial-grade aqueous formaldehyde solution, for example as a 20 to 50 wt%. solution, or in polymerized form, for example as trioxane and particularly paraformaldehyde. It is preferred to use commercial-grade aqueous formaldehyde solutions.

The reaction is generally carried out without the addition of basic reagents. It is also possible however to carry out the ethynylation in the presence of basic reagents. Examples of suitable basic reagents are salts of carboxylic acids, carbonates, hydroxides of the alkaline earth metals or of the alkali metals. Specific examples are potassium formate, sodium acetate, sodium carbonate, potassium carbonate, magnesium carbonate, and calcium hydroxide. The basic reagent may be used for example in dissolved form in the reaction mixture.

The starting material having the lower boiling point is used in gaseous form and the starting material with the higher boiling point is supplied in liquid form. Ethynylations are carried out generally at temperatures of from $-10°$ to $120°$ C., particularly of from $-10°$ C. to $100°$ C.

Generally the starting materials are reacted in a molar ratio of about 1:1. It is also possible however to use one of the starting materials in excess, and it is advantageous to maintain a molar ratio of the starting materials of from 1:1 to 1:10, particularly from 1:1 to 1:3.

When the new process is used for catalytic hydrogenation, the conventional hydrogenation catalysts may be used, e.g. metallic platinum, palladium, rhodium, ruthenium, nickel or cobalt, advantageously applied to carriers such as animal charcoal, barium sulfate, calcium carbonate, silica gel or aluminum oxide. The new method may be used for carrying out conventional catalytic hydrogenations, for example the hydrogenation of carbon-carbon triple bonds to corresponding double or saturated bonds, the hydrogenation of double bonds, the hydrogenation of aromatic hydrocarbons to cycloaliphatic hydrocarbon, of carbonyl groups to hydroxyl groups, of nitro groups to amino groups, of nitrile compounds to amines, of amine oxide groups to amines, the hydrogenolysis of protected groups such as benzyl ester or benzyl ether groups, and the hydrogenolysis of acid chlorides to aldehydes.

Hydrogenation may be carried out in the absence of solvents. It is also possible however to carry it out in the presence of liquids conventionally used for catalytic hydrogenations, such as ethers, esters, lower aliphatic carboxylic acids, alcohols or water. Temperatures of for example from $10°$ to $300°$ C. and pressure to 325 atmospheres may be used for the catalytic hydrogenation according to the invention. It is also possible however to use subatmospheric pressure, for example 600 mm Hg.

The following Examples illustrate the invention.

EXAMPLE 1

This Example is given with reference to FIG. 2. A pressure-resistant packed column 1 of stainless steel having a length of 6 meters and a diameter of 45 mm is used for the reaction. The packed column is filled with a supported catalyst shaped in the form of pellets 3 mm in diameter 2.5 to 3 mm in length. The analysis of the catalyst is as follows: 85% by weight of silica gel, 12% by weight of CuO and 3% by weight of bismuth. 1 liter per hour of 37% by weight aqueous formaldehyde solution 11 is fed in through line 11a and 170 liters (STP) per hour of acetylene 9 is fed in through line 9a. Recycled reaction liquid is supplied through line 12 and recycled acetylene gas is supplied through line 13 to the packed column. After they have passed through the packed column, separation of the acetylene phase from the liquid reaction mixture is carried out in a separator 2. 114 liters per hour of the liquid reaction mixture is withdrawn from the separator 2 through outlet 17 by way of circulation pump 3 and flow meter 6 and recycled through a circulation cooler 5. Some of the liquid reaction mixture is withdrawn from the separator 2 through line 14 as reaction product. Unreacted acetylene gas is recycled in an amount of 750 liters (STP) per hour from the separator 2 through line 16, circulation pump 4 and flow meter 7. Some of the recycled gas is withdrawn through line 10a as offgas. The difference in pressure between supply line and discharge line of the column is measured by means of a differential pressure meter 8 and is 1.2 atmospheres gauge. At an acetylene pressure of 5 atmospheres gauge the reaction temperature in the packed column is 105° C. 50 liters (STP) of offgas 10 per hour is withdrawn at 10a. 1.2 liters per hour of reaction product 15 is removed from the separator; it has a formaldehyde content of 10% by weight. The yield of butynediol is 97% of the theory, based on formaldehyde reacted. The conversion of formaldehyde is 73%. During the reaction under the said conditions, the whole packed column is traversed by an intimate mixture of acetylene gas and reaction liquid in transition flow. No decline in activity of the catalyst is observed in the said apparatus using the same catalyst even after sixty days.

If however pump 3 for circulating the liquid is switched off so that the flow regime in the column is that of gas continuous flow, the catalyst becomes encrusted within a short time and is completely inactive after only twenty-four hours.

EXAMPLE 2

The apparatus described in Example 1 in which an additional separating vessel arranged downstream of the circulation cooler 15 is used for the reaction. The packed column 1 described in Example 1 is filled with a supported catalyst in the form of pellets 4 mm in diameter and 3 to 8 in length, analysis of which gives a content of 25% by weight of nickel and 75% by weight of silica gel. 1 liter per hour of nitrobenzene is supplied through line 11a and 650 liters (STP) per hour of hydrogen through line 9a. 1.1 m³ (STP) of reacted hydrogen gas and 130 liters of liquid reaction mixture per hour are recycled through the column analogously to Example 1. The hydrogen pressure is 100 atmospheres gauge and the reaction temperature in the packed column is 100° C. 50 liters (STP) of offgas is withdrawn per hour. The pressure difference between the upper and lower ends of the column is 1 atmosphere. Entrained water of reaction is deposited in a separating vessel arranged downstream of the circulation cooler 5. 1.3 liters per hour of reaction product (water and aniline) is withdrawn from the separator. This has a nitrobenzene content of 0.1%. The yield of aniline is 99.9% based on reacted nitrobenzene. The conversion of nitrobenzene is 99.9%. There is no decline in hydrogenation efficiency even after fourteen days in the said apparatus using the same catalyst.

When the pump 6 for recycling the liquid is switched off, however, and the flow regime in the column is that of gas continuous flow, the temperature in the column rises immediately to more than 200° C. and a mixture of completely hydrogenated and cracked products is obtained.

EXAMPLE 3

The apparatus described in Example 1 is used but the packed column described is replaced by a glass tube having an internal diameter of 40 mm and a length of 2 meters. This is filled with 2.55 liters of a catalyst consisting of pellets having a diameter of 2 mm and a length of 2 to 6 mm and consisting of 0.5% of palladium and 99.5% of silica gel. 1 liter per hour of 25% by weight solution of trimethyl-p-benzoquinone in isobutyl alcohol is pumped in through line 11a 50 liters (STP) of hydrogen is supplied per hour through line 9a. 120 liters per hour is passed through the liquid circulation and 125 liters (STP) per hour through the gas circulation. The pressure drop is 220 mm Hg. Hydrogenation is carried out at atmospheric pressure and a temperature of 90° C. 20 liters (STP) of offgas is withdrawn per hour. 1.0 liter per hour of reaction solution is withdrawn from the separator; it contains 25% of trimethylhydroquinone. The conversion and yield are practically 100% of the theory.

If the circulation pump is switched off so that the flow regime in the column is that of gas continuous flow, the originally water-clear solution of trimethylhydroquinone flowing out becomes brown to black within three hours by reason of the formation of quinhydrone.

Dependence of the Pressure Difference Δp on the Liquid Loading of the Packed Column (L)

The following apparatus (cf. FIG. 3) is used to measure the dependence of the pressure difference Δp on the liquid loading L of the packed column. A glass tube 1 having a length of 130 cm and an internal width of 45 mm is filled over a length of 120 cm with glass spheres having a diameter of 3 mm. The glass spheres are supported at the lower end of the column by a sieve having a mesh width of 1.5 mm. The outlet has a cross-section which is larger than the free cross-section available between the spheres so that no additional pressure can be produced by the build-up of gas and liquid in the outlet. Measurement of the amount of gas and liquid supplied is carried out by means of flowmeters (Rotameters) 7 and 6. The pressure difference Δp is measured in a manometer 8. To measure the pressure difference Δp, in case the amount of hydrogen (9) is kept constant and the liquid loading L is slowly increased, water being used as the liquid. Dependence of the pressure difference Δp on the amount of liquid L at different amounts of gas (which are however kept constant in each case) is shown in FIG. 1.

We claim:

1. In a process for carrying out a solid-catalyst promoted exothermic reaction between a gas and a liquid, wherein the gas and the liquid are conducted cocurrently through a packed column, the solid catalyst serving, alone or in admixture with inert packing, as the packing and wherein a pressure drop $\Delta p$ is observed between the ends of said column, the improvement which comprises passing an intimate mixture of the gas and the liquid in the form of a turbulent stream through the packed column at such rates that, when the gas flow rate is kept constant, a variation in flow rate of the liquid produces a rise in the pressure difference $\Delta p$ with increasing liquid flow load L, expressed as $\Delta p/L$, at least twice as large as the rise $\Delta p/L$ under liquid trickling conditions providing laminar flow of the liquid over the packing bodies and continuous gas flow but said liquid flow rate being below the rate at which pulsing $\Delta p$ in the column is produced, said packing being spheres having diameters of 2 to 8 mm., cylindrical bodies having a length of 2 to 15 mm. and a diameter of 2 to 6 mm. or nonspherical or non-cylindrical bodies having a volume equivalent to that of said spheres.

2. A process as claimed in claim 1 wherein said reaction is an exothermic reaction, and the temperature throughout said column fluctuating by not more than ±20° C.

3. A process as claimed in claim 1 wherein said reaction is an exothermic reaction, and the temperature throughout said column fluctuating by not more than ±5° C.

4. A process as claimed in claim 1 wherein said process is one for the production of alkynols and/or alkynediols by reaction of a gaseous acetylene with an aldehyde in the liquid in the presence of a heavy metal acetylide catalyst in said packing.

5. A process as claimed in claim 1 wherein said process is one for the production of butynediol by the reaction of gaseous acetylene with formaldehyde in aqueous solution in the presence of a heavy metal aceytlide catalyst in said packing.

6. A process as claimed in claim 5 wherein a basic reagent is present in the reaction medium in the packed column.

7. A process as claimed in claim 1 wherein said intimate mixture of said liquid and said gas is passed downwardly through a vertical, packed column in the form of a turbulent stream.

8. A process as claimed in claim 1 wherein said process is catalytic hydrogenation carried out with hydrogen gas and a solid, hydrogenation catalyst in said packing.

9. A process as claimed in claim 1, separating the gas and liquid reaction product in a separator, and recycling a portion of the separated liquid reaction product back to said column.

10. A process as claimed in claim 1 wherein said column is a vertical, cylindrical column having a length to diameter ratio of 2:1 to 100:1.

11. A process as claimed in claim 1, wherein said packing comprises spheres having diameters of 2 to 8 mm.

12. A process as claimed in claim 1, wherein said packing comprises cylindrical bodies having a length of 2 to 15 mm. and a diameter of 2 to 6 mm.

13. A process as claimed in claim 1 wherein the liquid and gas flow rate through said column are chosen by the steps of measuring a series of pressure drops $\Delta p$ between the ends of said column while flowing said gas through a packed column or columns at one or more, constant gas flow rate, and while keeping each gas flow rate constant, passing said liquid cocurrently through said column or columns first at a relatively low rate and thereafter at increasing liquid flow rates under conditions in said column ranging from trickling liquid, continuous gas flow through turbulent flow of said intimate mixture of the gas and liquid through the column, and determining from the series of measured pressure drops (a) $\Delta p/L$ values under said liquid trickling conditions and (b) $\Delta p/L$ values for the turbulent stream, from which values the liquid and gas flow rates for the process are chosen.

* * * * *